(12) United States Patent
Best

(10) Patent No.: US 10,307,134 B1
(45) Date of Patent: Jun. 4, 2019

(54) STETHOSCOPE WITH LED INDICATOR STEM

(71) Applicant: James Best, Hollis, NH (US)

(72) Inventor: James Best, Hollis, NH (US)

( * ) Notice: Subject to any disclaimer, the term of this patent is extended or adjusted under 35 U.S.C. 154(b) by 0 days.

(21) Appl. No.: 16/124,241

(22) Filed: Sep. 7, 2018

Related U.S. Application Data

(60) Provisional application No. 62/557,508, filed on Sep. 12, 2017.

(51) Int. Cl.
*A61B 5/00* (2006.01)
*A61B 7/04* (2006.01)
*G08B 5/38* (2006.01)
*A61B 5/024* (2006.01)

(52) U.S. Cl.
CPC ............ *A61B 7/04* (2013.01); *A61B 5/02444* (2013.01); *A61B 5/746* (2013.01); *G08B 5/38* (2013.01); *A61B 2560/0214* (2013.01)

(58) Field of Classification Search
CPC ............................. A61B 7/02; A41D 13/0012
USPC ....................................................... 340/573.1
See application file for complete search history.

(56) References Cited

U.S. PATENT DOCUMENTS

| 2,142,407 | A | 1/1939 | Norton et al. |
|---|---|---|---|
| 6,016,844 | A | 1/2000 | Takahashi et al. |
| 7,527,123 | B2 | 5/2009 | Puder |
| 8,092,396 | B2 | 1/2012 | Bagha et al. |
| 8,548,174 | B2 | 10/2013 | Dufresne et al. |
| 2004/0249298 | A1* | 12/2004 | Selevan .................. A61B 5/024 600/528 |
| 2006/0260865 | A1* | 11/2006 | Puder ....................... A61B 7/02 181/131 |
| 2010/0056956 | A1* | 3/2010 | Dufresne ................. A61B 7/04 600/586 |
| 2011/0121141 | A1 | 5/2011 | Tatsuta et al. |
| 2016/0100817 | A1 | 4/2016 | Hussain |

* cited by examiner

*Primary Examiner* — Fabricio R Murillo Garcia
(74) *Attorney, Agent, or Firm* — Thomas M. Joseph, Esq

(57) ABSTRACT

An earpiece assembly has a pair of earpieces, a pair of foldable flex spring members, and a manifold with each foldable flex spring member connecting one of the earpieces to the manifold. A drum assembly has a diaphragm mounted therein and a tube extending therefrom with the diaphragm being particularly adapted to expand and contract in response to pressure changes within a patient when the drum assembly is in proximity to the patient. A stem assembly has a housing, a pressure sensor extending from the housing, a circuit board positioned within the housing, and a light source connected to the circuit board and extending from the housing. The stem assembly connects the manifold to the tube to connect the earpiece assembly to the drum assembly. The pressure sensor measures responses to pressure changes within the drum assembly and communicates with the circuit board, so that the circuit board can activate the light source to produce a flashing light pattern that corresponds to pressure changes within the patient.

18 Claims, 5 Drawing Sheets

STETHOSCOPE WITH LED INDICATOR STEM

CROSS REFERENCE TO RELATED APPLICATION

This application claims the benefit under 35 U.S.C. § 119(e) of U.S. Provisional Application No. 62/557,508 entitled "STETHOSCOPE WITH LED INDICATOR STEM" filed Sep. 12, 2017, which is incorporated herein by reference.

BACKGROUND

Stethoscopes are useful tools in medical examination, testing, and diagnosis that can assist with the determination of the physical health of a patient as well as to determine the extent of any pathologies. Stethoscopes can be used to examine biological systems, such as the cardiovascular, respiratory, and/or gastrointestinal systems. Stethoscopes are particularly useful for the measurement of heart rates, but can be used for listening to the internal sounds within the body of a subject.

FIG. 1 illustrates a conventional stethoscope 10 that can be used to measure a heart rate, as well as other internal noises within a patient. The stethoscope 10 has a pair of plastic earpieces 12 attached to a "Y" shaped tubing system 14 having a pair of essentially rigid metal binaurals 16 extending therefrom. In this conventional stethoscope 10, the metal binaurals 16 typically have a flexible opaque acoustic tubing 18 over a bottom shaft 20. Other conventional stethoscopes can include a single earpiece.

The bottom shaft 20 extends from an end 22 of the metal binaurals 16 for approximately 18 inches to a drum assembly or chestpiece 24. The drum assembly 24 includes an internal diaphragm or drum 26 that can expand or contract in responses to internal pressure changes within a patient when the drum assembly 24 is placed in close proximity to the patient. The drum assembly 24 can be referred to as the "bell end" of the stethoscope 10.

The drum assembly 24 further includes a threaded member 28 that extends into the acoustic tubing 18 to connect the drum assembly 24 to the tubing system 14. The acoustic tubing 18 can be used to transmit acoustic sounds through the stethoscope 10 to the metal binaurals 16.

The proper use of a stethoscope, such as the stethoscope 10 shown in FIG. 1, requires substantial clinical experience, and an environment that permits clear hearing. Heart sounds, for example, can sound rather faint through the stethoscope 10. The acoustic tubing 16 can create extraneous noise when the tubes rub against hands, body, or clothing, etc. Additionally, the stethoscope 10 poorly accommodates those with moderate to severe hearing loss, or those who work in noisy environments (e.g., emergency rooms, helicopters, etc.).

In view of the above, improved devices and methods of are needed to reduce inaccuracies that result from, inter alia, extraneous noises when a stethoscope operator measures the breathing rate, heart rate or pulse rate of a patient.

SUMMARY

The following summary is provided to introduce a selection of concepts in a simplified form that are further described below in the detailed description. This summary is not intended to identify key features or essential features of the claimed subject matter, nor is it intended to be used to limit the scope of the claimed subject matter.

In various implementations, a stethoscope has an earpiece assembly at one end, a drum assembly at the other end, and a stem assembly positioned between the earpiece assembly and the drum assembly. The drum assembly includes a diaphragm therein that is particularly adapted to expand and contract in response to pressure changes within a patient when the drum assembly is in proximity to the patient. The earpiece assembly includes a first tube extending therefrom and the drum assembly includes a first member extending therefrom. The stem assembly includes a housing having a second member for inserting into the ear assembly first tube and a second tube for receiving the drum assembly first member to connect the ear assembly to the drum assembly. A pressure sensor is positioned within the housing for measuring responses to pressure changes when the drum assembly is in proximity to the patient and for producing output that corresponds to the pressure changes. A circuit board is positioned within the housing and is coupled to the pressure sensor and has a light source extending therefrom. The circuit board receives the pressure sensor output and flashes the light source in response to the pressure sensor output to produce a flashing light pattern that corresponds to pressure changes within the patient.

In other implementations, a stethoscope includes an earpiece assembly having a pair of earpieces, a pair of foldable flex spring members, and a manifold with each foldable flex spring member connecting one of the earpieces to the manifold. A drum assembly has a diaphragm mounted therein and a tube extending therefrom with the diaphragm being particularly adapted to expand and contract in response to pressure changes within a patient when the drum assembly is in proximity to the patient. A stem assembly has a housing, a pressure sensor extending from the housing, a circuit board positioned within the housing, and a light source connected to the circuit board and extending from the housing. The stem assembly connects the manifold to the tube to connect the earpiece assembly to the drum assembly. The pressure sensor measures responses to pressure changes within the drum assembly and communicates with the circuit board, so that the circuit board can activate the light source to produce a flashing light pattern that corresponds to pressure changes within the patient.

These and other features and advantages will be apparent from a reading of the following detailed description and a review of the appended drawings. It is to be understood that the foregoing summary, the following detailed description and the appended drawings are explanatory only and are not restrictive of various aspects as claimed.

DETAILED DESCRIPTION

Figure 1:
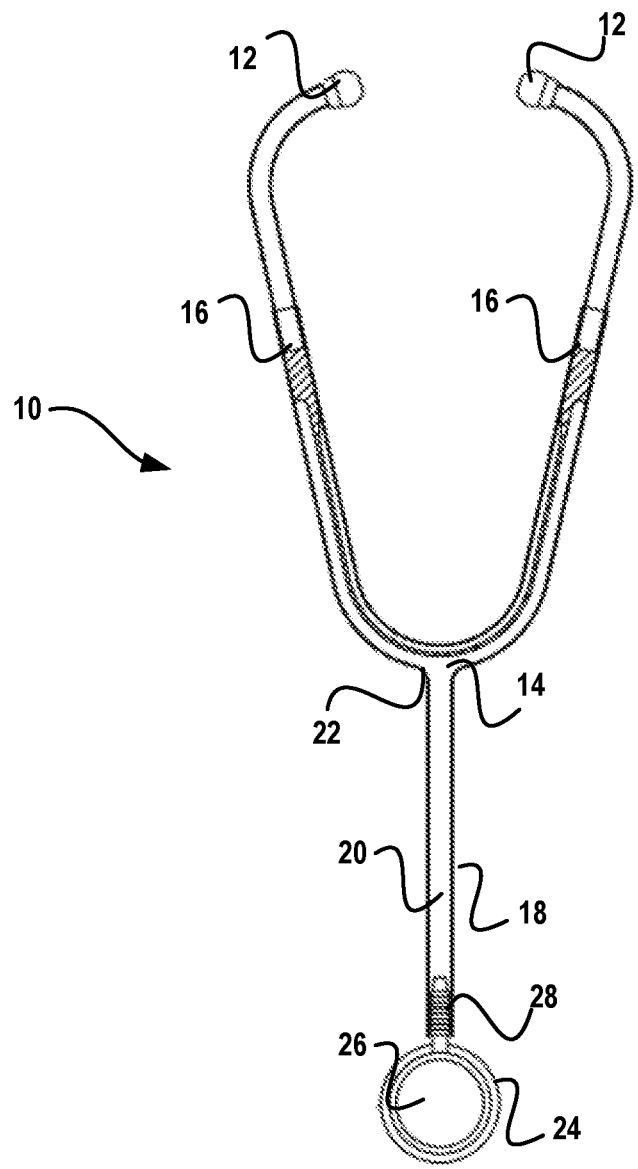
FIG. 1 is a sectional view of a stethoscope found in the prior art.

The subject disclosure is directed to new and improved portable stethoscope. The improved stethoscope includes an accessory device that can be attached to or can be retrofitted to most existing stethoscopes to produce lights patterns that correspond to the heartbeat of a patient or to other internal noises for the patient. The improved stethoscope further includes a pair of flex spring members, so that the stethoscope can be more easily folded into a jacket pocket, a pants pocket, a carrying case, or an envelope. As a result, the stethoscope can stay cleaner.

The detailed description provided below in connection with the appended drawings is intended as a description of examples and is not intended to represent the only forms in which the present examples can be constructed or utilized. The description sets forth functions of the examples and sequences of steps for constructing and operating the examples. However, the same or equivalent functions and sequences can be accomplished by different examples.

References to "one embodiment," "an embodiment," "an example embodiment," "one implementation," "an implementation," "one example," "an example" and the like, indicate that the described embodiment, implementation or example can include a particular feature, structure or characteristic, but every embodiment, implementation or example can not necessarily include the particular feature, structure or characteristic. Moreover, such phrases are not necessarily referring to the same embodiment, implementation or example. Further, when a particular feature, structure or characteristic is described in connection with an embodiment, implementation or example, it is to be appreciated that such feature, structure or characteristic can be implemented in connection with other embodiments, implementations or examples whether or not explicitly described.

Numerous specific details are set forth in order to provide a thorough understanding of one or more embodiments of the described subject matter. It is to be appreciated, however, that such embodiments can be practiced without these specific details.

Various features of the subject disclosure are now described in more detail with reference to the drawings, wherein like numerals generally refer to like or corresponding elements throughout. The drawings and detailed description are not intended to limit the claimed subject matter to the particular form described. Rather, the intention is to cover all modifications, equivalents and alternatives falling within the spirit and scope of the claimed subject matter, The disclosed subject matter is directed to a simple stethoscope device that augments a practitioner's auditory capabilities using a flashing light source when monitoring vital signs for a patient. The stethoscope can be used as a teaching tool or in EMT or EMF field situations where it is difficult for the practitioner to hear the sounds emanating from a conventional stethoscope.

The improved stethoscope is particularly useful in hospital and similar environments where doctors, nurses, EMT technicians, and other practitioners are encouraged to remove the stethoscope from around their necks when the stethoscope is not in use. Such stethoscopes include can flex spring members that are foldable in one direction, which provides the flex spring member with the ability to be stiff in one direction and to be folded in another direction.

Figure 2:
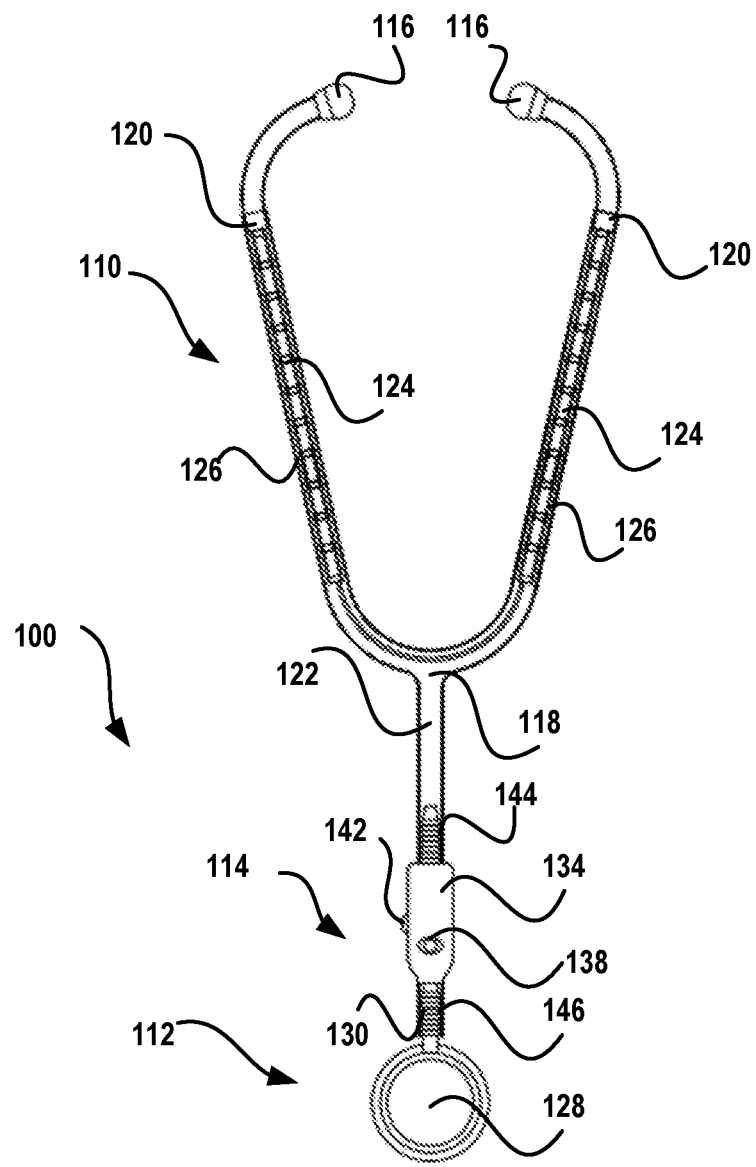
FIG. 2 is a sectional view of an improved stethoscope in accordance with the described subject matter.
Figures 3, 4:
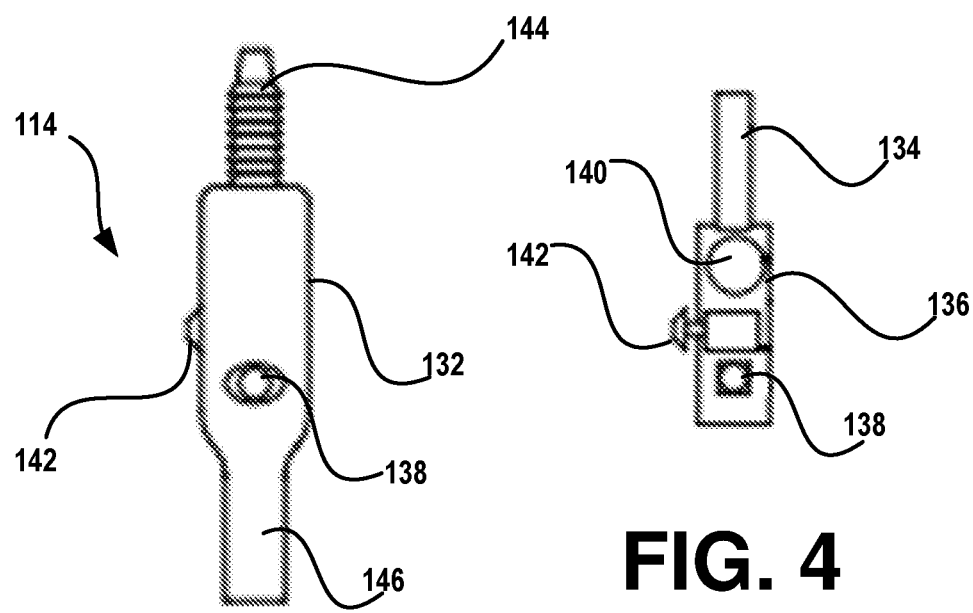
FIG. 3 is a side elevation view of a stem assembly for the improved stethoscope shown in FIG. 2.
FIG. 4 is a side elevation view of an assembled pressure sensor, circuit board, and light source that can be inserted into a housing for the stem assembly shown in FIG. 3.

Referring to FIGS. 2-4 with continuing reference to the foregoing figure, an improved stethoscope, generally designated by the numeral 100, is shown. Like the stethoscope 10 shown in FIG. 1, the stethoscope 100 can be used to measure a heart rate, as well as other internal noises within a patient. The stethoscope 100 includes an earpiece assembly 110, a drum assembly 112, and a stem assembly 114.

Unlike the stethoscope 10 shown in FIG. 1, the stem assembly 114 connects the earpiece assembly 110 to the drum assembly 112. The stem assembly 114 can be a compact, standalone component that is particularly adapted to produce a flashing light pattern that corresponds to pressure changes within the patient. The stem assembly 114 can be sold or distributed as an accessory device that can be attached to or can be retrofitted to most existing stethoscopes, including the stethoscope 10 shown in FIG. 1.

The earpiece assembly 110 includes a pair of earpieces 116, a "Y" shaped tubing assembly 118, a pair of binaurals 120, a manifold 122, a pair of flex spring members 124, and flexible tubing 126. The pair of plastic earpieces 116 is attached to the "Y" shaped tubing system 118, which includes the pair of binaurals 120 extending therefrom. The "Y" shaped tubing system 118 includes the manifold 122.

Unlike the stethoscope 10 shown in FIG. 1, each of the binaurals 120 includes the flex spring member 124 for connecting the earpieces 116 to the manifold 122. The flex spring members 124 are covered by the flexible tubing 126. In an alternative embodiment, the "Y" shaped tubing system 118 includes the flex spring members 124 and the flexible tubing 126 connecting the earpieces 116 to the manifold 122, but the flex spring members 124 are not covered by the flexible tubing 126.

Like the stethoscope 10, the stethoscope 100 includes a drum assembly 112 that is essentially identical to the drum assembly 24 shown in FIG. 1. The drum assembly 112 has a diaphragm or a drum 128 mounted therein and a tube 130 extending therefrom. The drum 128 is particularly adapted to expand and contract in response to pressure changes within a patient when the drum assembly 112 is in proximity to a patient. The drum assembly 112 has a threaded member 130 that extends from the drum assembly 112 to connect the drum assembly 112 to the stem assembly 114.

The stem assembly 114 has a housing 132, a sensor 134, a circuit board 136, a flashing light source 138, a power supply or a power source 140, and an on/off switch 142. The sensor 134 has an essentially cylindrical threaded tubular member 144 extending from the housing 132 into the manifold 122 in this exemplary embodiment. In other exemplary embodiment, the member 144 extends from the sensor 134 extends into the drum assembly 112. Alternatively, the sensor 134 can be positioned entirely within the housing 132, as long as the manifold 122 and/or the drum assembly 112 are in fluid communication with the housing 132.

The circuit board 136 can be positioned within the housing 132. The light source 138 can extend from the circuit board 136 and can be inserted through the housing 132, so that it is externally visible when it flashes. The circuit board 136 can connect the sensor 134 to the light source 138, so that the sensor 134 can send electrical and/or electronic signals to activate the light source 138. The circuit board 136 can convert output from the sensor 134 to the signals that activate the light source 138. The on/off switch 142 is configured to turn the circuit board 136 on or off.

The power supply or the power source 140 can be any suitable power source or power supply, such as a compact standalone internal power source or a power cord connected to an external power supply or power supply system. In this exemplary embodiment, the power source 140 is a battery. Similarly, the light source 138 can be any suitable light source, such as an LED, including a light source that includes multiple lights for producing a predetermined light pattern or series of light patterns.

In operation, the tubular member 144 inserts into the manifold 122 to connect the stem assembly 114 to the earpiece assembly 110. The threaded member 130 inserts into a receiving member 146 that extends from the housing 132 to connect the stem assembly 114 to the drum assembly 112. Upon assembly, the sensor 134 is coupled to the drum assembly 112 for detecting internal noises, including a heartbeat, within a patient. In this exemplary embodiment, the sensor 134 is a pressure sensor that measures responses to pressure changes within the drum assembly 112 and communicates with the circuit board 136, so that the circuit board 136 can activate the light source 138 to produce a flashing light pattern that corresponds to internal noises and/or pressure changes within the patient.

The circuit board 136 can be programmed to activate the light source 138 display different light patterns that correspond to different internal noises that correspond to different sound waves or internal pressure differences within a patient. In some embodiments, the circuit board 136 can include an external connector or network connection (not shown) to facilitate programming or allow for the downloading or uploading of data, data structures, software instructions, applications, programs, modules, etc.

The flashing of the light source 138 can be used by a doctor, nurse, EMT technician or other practitioner to listen and to see noises within a patient. The visual aspect of this disclosed feature can be used to augment the ability of the practitioner to monitor a patient's vital signs. These features can be used as a teaching tool or in a field situation where it is difficult for the practitioner to hear the sounds emanating from the stethoscope 100.

The stethoscope 100 can be packaged and sold as a single kit with the earpiece assembly 110, a drum assembly 112, and a stem assembly 114 being individual components of the kit. Alternatively, the earpiece assembly 110, a drum assembly 112, and a stem assembly 114 can be sold individually, with other components, or in various combinations, thereof.

Figure 5A:
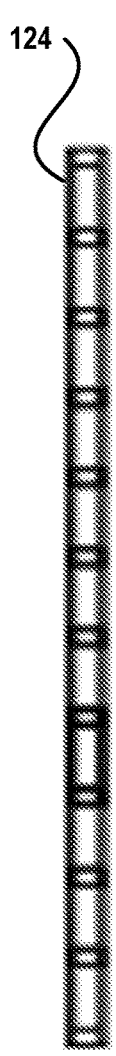
FIG. 5A is a sectional view of a tubular member that holds a foldable flex spring assembly in accordance with the described subject matter.
Figure 5B:
FIG. 5B is a side elevation view of the foldable flex spring assembly shown in FIG. 5A in an unfolded configuration.
Figure 5C:
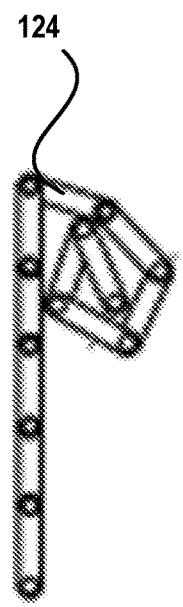
FIG. 5C is a side elevation view of the foldable flex spring assembly shown in FIG. 5A in a folded configuration.

Referring to FIGS. 5A-5C with continuing reference to the foregoing figures, the flex spring member 124 shown in FIG. 2 is shown in various configurations. FIGS. 5A-5B shows different views of the flex spring member 124 in an unfolded configuration. FIG. 5C shows the flex spring member 124 in a partially folded configuration. As shown in FIGS. 5A-5C, the flex spring member 124 is foldable in one direction. The ability to fold and unfold the flex spring member 124 in this manner provides the flex spring member 124 with the ability to be stiff in one direction and to be folded in another direction, so that the stethoscope 100 shown in FIGS. 2-4 can be more easily folded into a jacket pocket, a pants pocket, or a carrying case.

The flex spring member 124 can provide the stethoscope 100 with the ability to be folded up into an envelope. The use of the flex spring member 124 in the stethoscope 100 shown in FIGS. 2-4 encourages hospital workers to put the stethoscope away when they are not being used, so that the stethoscope 100 can stay cleaner. The use of the flex spring member 124 provides the stethoscope 100 with improved portability.

Figure 6:
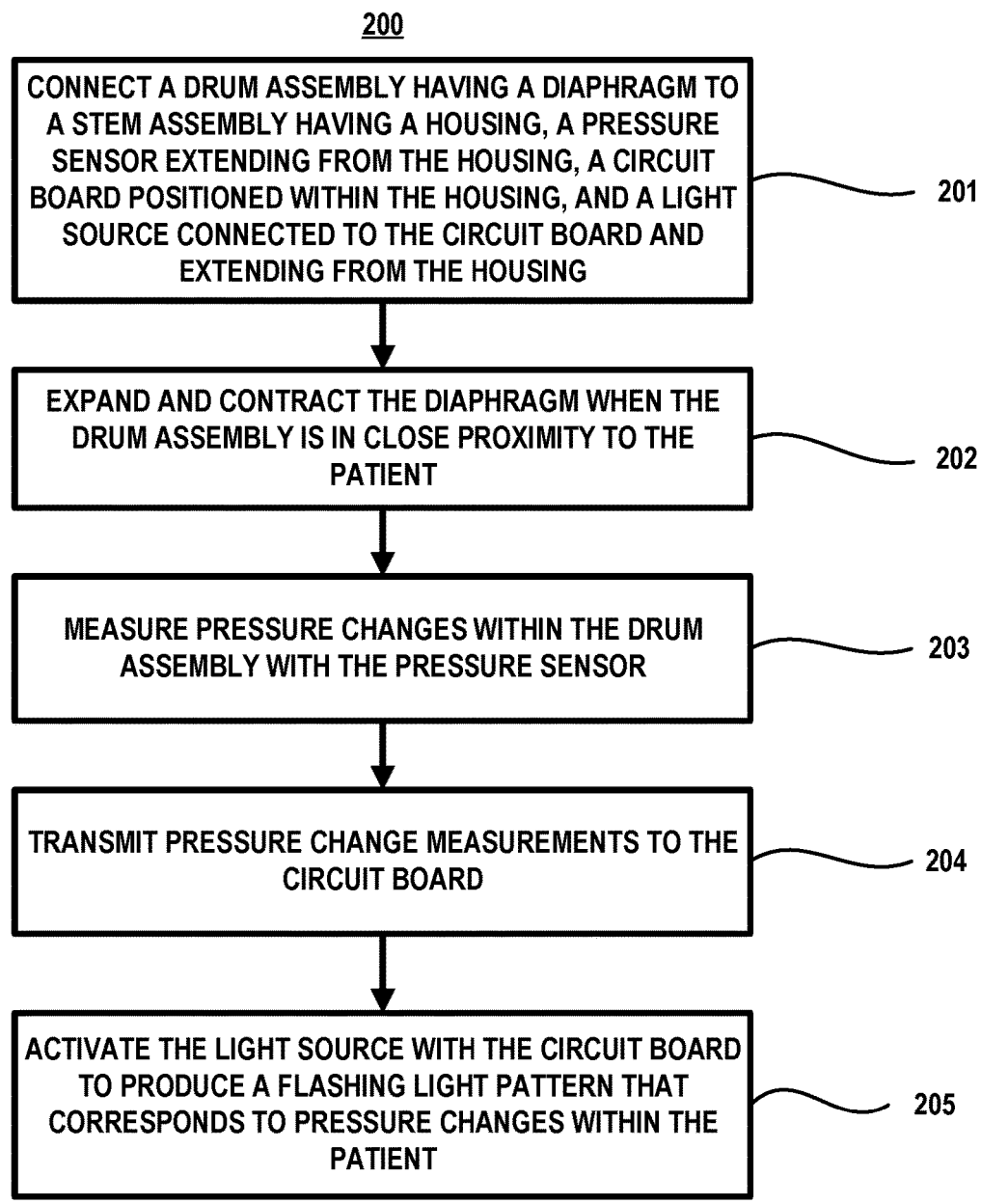
FIG. 6 illustrates an embodiment of an exemplary process in accordance with the described subject matter.

Referring to FIG. 6 with continuing reference to the foregoing figures, a method 600 for monitoring the heartbeat of a patient in accordance with aspects of the described subject matter is shown. Method 600, or portions thereof, can be performed using the various embodiments of stethoscopes, such as stethoscope 100, shown in FIGS. 2-4.

At 601, a drum assembly having a diaphragm is connected to a stem assembly having a housing, a pressure sensor extending from the housing, a circuit board positioned within the housing, and a light source connected to the circuit board and extending from the housing. In this exemplary embodiment, the stem assembly is the stem assembly 114 shown in FIG. 2. The housing, the pressure sensor, the circuit board, and the light source are the housing 132, the sensor 134, the circuit board 136, and the light source 138 shown in FIGS. 2-4.

At 602, the diaphragm is expanded and contracted when the drum assembly is in close proximity to the patient. In this exemplary embodiment, the diaphragm is the diaphragm shown in FIG. 2.

At 603, pressure changes within the drum assembly are measured with the pressure sensor. In this exemplary embodiment drum assembly is the drum assembly 112 shown in FIG. 2.

At 604, transmitting pressure change measurements to the circuit board. In this exemplary embodiment, the pressure change measurements are transmitted to the circuit board 136 shown in FIGS. 2-4.

At 605, activating the light source with the circuit board to produce a flashing light pattern that corresponds to pressure changes within the patient. In this exemplary embodiment, the flashing light pattern is produced by the light source 138 shown in FIGS. 2-4. The circuit board 136 shown in FIGS. 2-4 activates the light source 138.

SUPPORTED FEATURES AND EMBODIMENTS

The detailed description provided above in connection with the appended drawings explicitly describes and supports various features of an improved stethoscope. By way of illustration and not limitation, supported embodiments include, in a stethoscope having an earpiece assembly at one end, a drum assembly at the other end, and a stem assembly positioned between the earpiece assembly and the drum assembly, wherein the drum assembly includes a diaphragm therein that is particularly adapted to expand and contract in response to pressure changes within a patient when the drum assembly is in proximity to the patient, wherein the earpiece assembly includes a first tube extending therefrom and the drum assembly includes a first member extending therefrom, the stem assembly comprising: a housing having a second member for inserting into the ear assembly first tube and a second tube for receiving the drum assembly first member to connect the ear assembly to the drum assembly, a pressure sensor positioned within the housing for measuring responses to pressure changes when the drum assembly is in proximity to the patient and for producing output that corresponds to the pressure changes, and a circuit board positioned within the housing, coupled to the pressure sensor and having a light source extending therefrom, wherein the circuit board receives the pressure sensor output and flashes the light source in response to the pressure sensor output to produce a flashing light pattern that corresponds to pressure changes within the patient.

Supported embodiments include the foregoing stem assembly, further comprising a power source for supplying power to the circuit board.

Supported embodiments include any of the foregoing stem assemblies, wherein the power source is a battery.

Supported embodiments include any of the foregoing stem assemblies, wherein the light source is an LED.

Supported embodiments include any of the foregoing stem assemblies, further comprising an on/off switch for turning the circuit board on or off.

Supported embodiments include a system, a method and/or means for implementing any of the foregoing improved stem assemblies or portions thereof.

Supported embodiments include a stethoscope comprising: an earpiece assembly having a pair of earpieces, a pair of foldable flex spring members, and a manifold with each foldable flex spring member connecting one of the earpieces to the manifold, a drum assembly having a diaphragm mounted therein and a tube extending therefrom with the diaphragm being particularly adapted to expand and contract in response to pressure changes within a patient when the drum assembly is in proximity to the patient, and a stem assembly having a housing, a pressure sensor extending from the housing, a circuit board positioned within the housing, and a light source connected to the circuit board and extending from the housing, wherein the stem assembly connects the manifold to the tube to connect the earpiece assembly to the drum assembly, wherein the pressure sensor measures responses to pressure changes within the drum assembly and communicates with the circuit board, so that the circuit board can activate the light source to produce a flashing light pattern that corresponds to pressure changes within the patient.

Supported embodiments include the foregoing stethoscope, further comprising a power source for supplying power to the circuit board.

Supported embodiments include any of the foregoing stethoscopes, wherein the power source is a battery.

Supported embodiments include any of the foregoing stethoscopes, wherein the light source is an LED.

Supported embodiments include any of the foregoing stethoscopes, further comprising an on/off switch for turning the circuit board on or off.

Supported embodiments include any of the foregoing stethoscopes, wherein the flex spring member can fold in a single direction.

Supported embodiments include any of the foregoing stethoscopes, wherein the manifold is Y-shaped and includes a pair of tubular members extending to the earpieces.

Supported embodiments include any of the foregoing stethoscopes, wherein each of the foldable flex spring members is positioned in a tubular member.

Supported embodiments include a system, a method and/or means for implementing any of the foregoing improved stethoscopes or portions thereof.

Supported embodiments include a method for monitoring a heartbeat for a patient comprising: connecting a drum assembly having a diaphragm to a stem assembly having a housing, a pressure sensor extending from the housing, a circuit board positioned within the housing, and a light source connected to the circuit board and extending from the housing, expanding and contracting the diaphragm when the drum assembly is in close proximity to the patient, measuring pressure changes within the drum assembly with the pressure sensor, transmitting pressure change measurements to the circuit board, and activating the light source with the circuit board to produce a flashing light pattern that corresponds to pressure changes within the patient.

Supported embodiments include the foregoing method, further comprising: connecting an earpiece assembly to the stem assembly.

Supported embodiments include any of the foregoing methods, wherein the earpiece assembly includes a pair of earpieces, a pair of foldable flex spring members, and a manifold with each foldable flex spring member connecting one of the earpieces to the manifold, so that the manifold connects the earpiece assembly to the stem assembly.

Supported embodiments include any of the foregoing methods, further comprising: supplying power to the circuit board.

Supported embodiments include any of the foregoing methods, further comprising: supplying power to the circuit board with a battery.

Supported embodiments include any of the foregoing methods, wherein the light source is an LED.

Supported embodiments include any of the foregoing methods, further comprising: turning the circuit board on and off using an on/off.

Supported embodiments include a system, an apparatus and/or means for implementing any of the foregoing methods or portions thereof.

Supported embodiments include a stethoscope kit comprising: an earpiece assembly having a pair of earpieces, a pair of foldable flex spring members, and a manifold with each foldable flex spring member connecting one of the earpieces to the manifold, a drum assembly having a diaphragm mounted therein and a tube extending therefrom with the diaphragm being particularly adapted to expand and contract in response to pressure changes within a patient when the drum assembly is in proximity to the patient, and a stem assembly having a housing, a sensor extending from the housing, a circuit board positioned within the housing, and a light source connected to the circuit board and extending from the housing, wherein the stem assembly has the ability to connect to the manifold to the tube to connect the earpiece assembly to the drum assembly, wherein the sensor has the ability to couple with the drum assembly to measure internal noises within a patient and communicate with the circuit board, so that the circuit board can activate the light source to produce a flashing light pattern that corresponds to the internal noises within the patient.

Supported embodiments include a system, an apparatus, a method and/or means for implementing the foregoing kit or portions thereof.

Supported embodiments include a stethoscope comprising: an earpiece assembly having a pair of earpieces, a manifold, and means for connecting the earpieces to the manifold, a stem assembly for connecting the manifold to the tube to connect the earpiece assembly to the drum assembly having a light source therein, means for detecting internal noises within a patient, and means for activating the light source to produce a flashing light pattern that corresponds to the internal noises within the patient.

Supported embodiments include a system, an apparatus, a method, a kit and/or means for implementing the foregoing stethoscope or portions thereof.

Supported embodiments include a stethoscope stem assembly comprising: a housing having a member extending from one end and a tube extending from the opposite end, a sensor positioned within the housing for measuring internal noises within a patient and for producing output that corresponds to the internal noises, a circuit board positioned within the housing, coupled to the sensor and having a light source extending therefrom, a power source for supplying power to the circuit board, and an on/off switch for turning the circuit board on or off, wherein the circuit board receives the pressure sensor output and flashes the light source in response to the sensor output to produce a flashing light pattern that corresponds to internal noises within the patient.

Supported embodiments include the foregoing stethoscope stem assembly, wherein the sensor is a pressure sensor.

Supported embodiments include any of the foregoing stethoscope stem assemblies, wherein the pressure sensor measures the heartbeat of a patient.

Supported embodiments include a system, an apparatus, a method, a kit and/or means for implementing the foregoing stethoscope stem assembly or portions thereof.

Supported embodiments include a stethoscope stem assembly consisting essentially of: a housing having a member extending from one end and a tube extending from the opposite end, a sensor positioned within the housing for measuring internal noises within a patient and for producing output that corresponds to the internal noises, a circuit board positioned within the housing, coupled to the sensor and having a light source extending therefrom, a power source for supplying power to the circuit board, and an on/off switch for turning the circuit board on or off, wherein the circuit board receives the pressure sensor output and flashes the light source in response to the sensor output to produce a flashing light pattern that corresponds to internal noises within the patient.

Supported embodiments include a system, an apparatus, a method, a kit and/or means for implementing the foregoing stethoscope stem assembly or portions thereof.

Supported embodiments include a stethoscope comprising: an earpiece assembly having a pair of earpieces, a pair of foldable flex spring members, and a manifold with each foldable flex spring member connecting one of the earpieces to the manifold, a drum assembly having a diaphragm mounted therein and a tube extending therefrom with the diaphragm being particularly adapted to expand and contract in response to internal noises within a patient when the drum assembly is in proximity to the patient, and a stem assembly having a housing, a sensor extending from the housing, a circuit board positioned within the housing, and a light source connected to the circuit board and extending from the housing, wherein the stem assembly connects the manifold to the tube to connect the earpiece assembly to the drum assembly, wherein the sensor is coupled with the drum assembly to measure internal noises within a patient and communicates with the circuit board, so that the circuit board can activate the light source to produce a flashing light pattern that corresponds to internal noises within the patient.

Supported embodiments include the foregoing stethoscope, further comprising a power source for supplying power to the circuit board.

Supported embodiments include any of the foregoing stethoscopes, wherein the power source is a battery.

Supported embodiments include any of the foregoing stethoscopes, wherein the light source is an LED.

Supported embodiments include any of the foregoing stethoscopes, further comprising an on/off switch for turning the circuit board on or off.

Supported embodiments include any of the foregoing stethoscopes, wherein the flex spring member can fold in a single direction.

Supported embodiments include any of the foregoing stethoscopes, wherein the manifold is Y-shaped and includes a pair of tubular members extending to the earpieces.

Supported embodiments include any of the foregoing stethoscopes, wherein each of the foldable flex spring members is positioned in a tubular member.

Supported embodiments include a system, a method, a kit and/or means for implementing the foregoing stethoscope or portions thereof.

Supported embodiments can provide various attendant and/or technical advantages in terms of improved efficiency and/or savings with respect to an accessory device that can be attached to or can be retrofitted to most existing stethoscopes to produce lights patterns that correspond to the heartbeat of a patient or to other internal noises for the patient.

Supported embodiments include a simple device that augments a practitioner's auditory capabilities using a flashing light source when monitoring vital signs for a patient. Supported embodiments include a device that can be used as a teaching tool or in EMT or EMF field situations where it is difficult for the practitioner to hear the sounds emanating from a stethoscope.

Supported embodiments include a stethoscope that is particularly useful in hospital and similar environments where doctors, nurses, EMT technicians, and other practitioners are encouraged to remove the stethoscope from around their necks when the stethoscope is not in use. Such stethoscopes include flex spring members that are foldable in one direction, which provides the flex spring member with the ability to be stiff in one direction and to be folded in another direction Supported embodiments include a stethoscope that can be more easily folded into a jacket pocket, a pants pocket, a carrying case, or an envelope. Supported embodiments include a stethoscope that can stay cleaner and that has improved portability.

The detailed description provided above in connection with the appended drawings is intended as a description of examples and is not intended to represent the only forms in which the present examples can be constructed or utilized.

It is to be understood that the configurations and/or approaches described herein are exemplary in nature, and that the described embodiments, implementations and/or examples are not to be considered in a limiting sense, because numerous variations are possible. In particular, it should be understood that the disclosed stem assembly can be used with stethoscopes that include a single earpiece. The specific processes or methods described herein can represent one or more of any number of processing strategies. As such, various operations illustrated and/or described can be performed in the sequence illustrated and/or described, in other sequences, in parallel, or omitted. Likewise, the order of the above-described processes can be changed.

Although the subject matter has been described in language specific to structural features and/or methodological acts, it is to be understood that the subject matter defined in the appended claims is not necessarily limited to the specific features or acts described above. Rather, the specific features and acts described above are presented as example forms of implementing the claims.

What is claimed is:

1. A stethoscope having an earpiece assembly at one end, a drum assembly at another end, and a stem assembly positioned between the earpiece assembly and the drum assembly, wherein the drum assembly of the stethoscope includes a mounted diaphragm that is particularly adapted to expand and contract in response to pressure changes within a patient when the drum assembly is in proximity to the patient for obtaining internal noises within the patient, wherein the earpiece assembly of the stethoscope includes a first tube extending along the earpiece assembly, and at least a foldable flex spring member mounted along the first tube, and the drum assembly further includes a first member extending along the drum assembly, the stem assembly of the stethoscope comprising:

a housing having a second member for inserting into the ear assembly first tube and a second tube for receiving the drum assembly first member to connect the ear assembly to the drum assembly, a pressure sensor positioned within the housing for measuring responses to pressure changes when the drum assembly is in proximity to the patient obtaining internal noises within the patient and for producing output that corresponds to the pressure changes, and a circuit board positioned within the housing, coupled to the pressure sensor and having a light source extending along the circuit board, wherein the circuit board receives the pressure sensor output and flashes the light source in response to the pressure sensor output to produce a flashing light pattern that corresponds to the pressure changes within the patient.

2. The stem assembly of claim 1, further comprising a power source for supplying power to the circuit board.

3. The stem assembly of claim 2, wherein the power source is a battery.

4. The stem assembly of claim 1, wherein the light source is a light emitting diode (LED).

5. The stem assembly of claim 1, further comprising an on/off switch for turning the circuit board on or off.

6. A stethoscope comprising:

an earpiece assembly having a pair of earpieces, a pair of foldable flex spring members, and a manifold with each foldable flex spring member of the pair of foldable flex spring members connecting one of the earpieces to the manifold, a drum assembly having a mounted diaphragm and a tube extending, along the drum assembly, with the mounted diaphragm being particularly adapted to expand and contract in response to pressure changes within a patient when the drum assembly is in proximity to the patient for obtaining internal noises within the patient, and a stem assembly having a housing, a pressure sensor extending from the housing, a circuit board positioned within the housing, and a light source connected to the circuit board and extending from the housing, wherein the stem assembly of the stethoscope connects the manifold to the tube to connect the earpiece assembly to the drum assembly, wherein the pressure sensor measures responses to pressure changes within the drum assembly, when the drum assembly is in proximity to the patient obtaining internal noises within the patient, and communicates with the circuit board, so that the circuit board can activate the light source to produce a flashing light pattern that corresponds to the pressure changes within the patient.

7. The stethoscope of claim 6, further comprising a power source for supplying power to the circuit board.

8. The stethoscope of claim 7, wherein the power source is a battery.

9. The stethoscope of claim 6, wherein the light source is a light emitting diode (LED).

10. The stethoscope of claim 6, further comprising an on/off switch for turning the circuit board on or off.

11. The stethoscope of claim 6, wherein each foldable flex spring member of the pair of foldable flex spring members can fold in a single direction.

12. The stethoscope of claim 6, wherein the manifold is Y-shaped and includes a pair of tubular members extending to the earpieces.

13. The stethoscope of claim 12, wherein each foldable flex spring member of the pair of foldable flex spring members is positioned in a tubular member.

14. A method for monitoring, with a stethoscope, heartbeats from a patient comprising:

connecting a drum assembly having a mounted diaphragm to a stem assembly having a housing, a pressure sensor extending from the housing, a circuit board positioned within the housing, and a light source connected to the circuit board and extending from the housing, connecting an earpiece assembly to the stem assembly of the stethoscope, wherein the earpiece assembly of the stethoscope includes a pair of earpieces, a pair of foldable flex spring members, and a manifold with each foldable flex spring member of the pair of foldable flex spring members connecting one of the earpieces to the manifold, so that the manifold connects the earpiece assembly to the stem assembly, expanding and contracting the mounted diaphragm when the drum assembly is in close proximity to the patient for monitoring the heartbeats from the patient, measuring pressure changes within the drum assembly with the pressure sensor when the drum assembly is in close proximity to the patient for monitoring the heartbeats from the patient, transmitting pressure change measurements to the circuit board, and activating the light source with the circuit board to produce a flashing light pattern that corresponds to the pressure changes within the patient related to the monitored heartbeats.

15. The method of claim 14, further comprising:

supplying power to the circuit board.

16. The method of claim 15, further comprising:

supplying the power to the circuit board with a battery.

17. The method of claim 14, wherein the light source is a light emitting diode (LED).

18. The method of claim 14, further comprising:

turning the circuit board on and off using an on/off switch.

* * * * *